United States Patent [19]

Igarasi et al.

[11] 3,933,790

[45] Jan. 20, 1976

[54] PHOSPHORYLXYLOSTASIN

[75] Inventors: Seizi Igarasi; Makoto Kida, both of Hyogo, Japan

[73] Assignee: Takeda Chemical Industries, Ltd., Osaka, Japan

[22] Filed: July 8, 1974

[21] Appl. No.: 486,454

[30] Foreign Application Priority Data

July 9, 1973   Japan.............................. 48-77260

[52] U.S. Cl.............. 260/210 AB; 195/28; 195/29; 195/96; 260/210 K; 260/234 R; 424/181
[51] Int. Cl.².......................................... C07H 15/22
[58] Field of Search....... 260/210 AB, 210 R, 210 K

[56] References Cited

UNITED STATES PATENTS

| 3,661,892 | 9/1972 | Shomura et al. | 260/210 AB |
| 3,792,037 | 2/1974 | Kawaguchi et al. | 260/210 AB |

*Primary Examiner*—Johnnie R. Brown
*Attorney, Agent, or Firm*—Wenderoth, Lind & Ponack

[57] ABSTRACT

Phosphoric acid esters of xylostasin, an intermediate for the synthesis of antibiotic deoxy-xylostasin or the like, are obtained by contacting xylostasin with cells or cell materials of microorganism belonging to the genus Escherichia or Pseudomonas which is resistant to xylostasin, in the presence of a phosphate donor.

3 Claims, No Drawings

PHOSPHORYLXYLOSTASIN

This invention relates to phosphorylxylostasin and more particularly 3'-and/or 5''-phosphoric acid esters of xylostasin and a process for production thereof.

Xylostasin is an antibiotic which possesses a broad antibacterial spectrum (Belgium Pat. No. 800257). Like other aminoglycoside antibiotics, however, xylostasin is not exempted from the emergence of resistant microorganisms. The present inventors conducted extensive research to obtain an antibiotic active against such resistant strains of microorganisms, and found that 1. New 3' and/or 5'' phosphoric acid esters of xylostasin are useful synthetic intermediates which can be converted to various xylostasin derivatives active against said resistant strains;
2. The phosphorylation of xylostasin at the 3'-position and/or 5''-position is effected by contacting xylostasin with cells or cell materials of certain microorganisms belonging to the genus Escherichia or Pseudomonas in the presence of a phosphate donor; and
3. Such microorganisms are those resistant to xylostasin without exception.

These findings were followed by further studies which have culminated in this invention. Thus, the main object of this invention is to provide phosphoric acid esters of xylostasin at the 3'-position and/or 5''-position, useful as an intermediate for the synthesis of xylostasin derivatives, e.g., deoxy-xylostasin.

Another object is to provide a process for the production of the phosphorylated xylostasin.

A further object of this invention will become apparent from the following descriptions.

These objects are realized by contacting xylostasin with cells or cell materials of a microorganism belonging to the genus Escherichia or Pseudomonas which is resistant to xylostasin, in the presence of a phosphate donor.

Xylostasin is an antibiotic of the formula

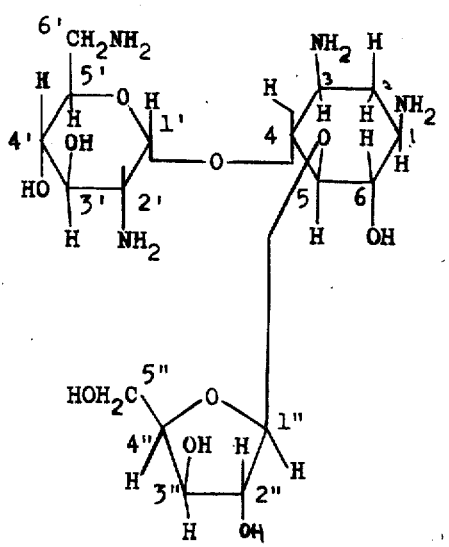

which can be obtained by cultivating a xylostasin-producing strain of a microorganisms of the genus Bacillus (Belgian Pat. No. 800257 and Reference Example 1 (B)) or by treating butirosin A with an alkali (Reference Example 1 (A)) to mention a few production methods.

In the phosphorylation of xylostasin, the hydroxyl groups in the 3'- and/or 5''-positions are specifically phosphorylated according to the characters of the microorganism to be employed. The microorganism to be employed in the practice of this invention is a bacterium which (1) belongs to the genus Escherichia or the genus Pseudomonas, and (2) is resistant to at least 100 $\mu$g. and generally 800 $\mu$g. of xylostasin per ml. medium. As examples, there may be mentioned *Escherichia coli* No. R11(FERM-P No. 2123, IFO 13560, ATCC 21990) and *Pseudomonas aeruginosa* No. R34R (FERM-P No. 2124, IFO 13561, ATCC 31040 ). The numbers in the parentheses with indications FERM-P, IFO and ATCC are the accession numbers at Fermentation Research Institute (FERM), the Agency of Industrial Science and Technology, Chiba, Japan; Institute for Fermentation, Osaka (IFO), Japan; and American Type Culture Collection (ATCC), Maryland, U.S.A., respectively.

*Escherichia coli* No. R11 is isolated from rat viscera, and its microbiological characteristics are as follows; Gram negative rod, motile, peritrichous flagella; acid and gas formed from glucose; methyl red test positive; Voges-Proskauer test positive, citrate not utilized; and indole formed.

*Pseudomonas aeruginosa* No. R34R has been isolated from a soil sample, and its microbiological characteristics are as follows; Gram negative rod, motile, polar flagella; catalase positive; oxidase positive; Hugh-Leifson test oxidative, acid produced from glucose; Litmus milk alkaline reaction; citrate utilized; indole not produced; and grows at 42°C.

These characteristics of *Escherichia coli* No. R11 and of *Pseudomonas aeruginosa* No. R34R are principally identical with those of the type strains of *Escherichia coli* and of *Pseudomonas aeruginosa*, respectively, as described in the Seventh Edition (1957) of Bergey's Manual of Determinative Bacteriology, except the present strains are resistant to xylostasin.

The process of this invention is carried out by contacting xylostasin with the cells or cell materials of the above-mentioned microorganisms. Such cells are obtained by propagating microorganisms in a medium containing as carbon sources, any one or more of glucose, sucrose, soluble starch, etc., and as nitrogen sources, any one or more of meat extract, yeast extract, cornsteep liquor, etc.; any of organic or inorganic nitrogen-containing materials such as amino acids, ammonium nitrate, ammonium chloride, etc.; and any of such inorganic materials as magnesium chloride, sodium chloride, etc. The cultivation is performed by the stationary cultural method or by the aerobic stirring cultural method. The incubation temperature is between 20°C and 45°C and preferably, between 20°C and 37°C; the pH range is from 6 to 9 and, preferably, from 6.8 to 7.8 and the cultivation time is 2 to 72 hours and, preferably, 6 to 24 hours.

The cells thus propagated in the culture broth are employed as such or as phosphotransferase-active cell materials or disrupted cells after processing.

The said disrupted cells or cell materials are obtainable by subjecting a culture broth as obtained in the above manner to any such physical or chemical treatments as, for example, filtration, centrifugation, ultrasonication, treatment by disintegrator, alumina grinding treatment with a bacteriolytic enzyme, treatment or extract with a surfactant or an organic solvent, etc.

The phosphorylation of xylostasin in the presence of a phosphate donor is conducted in a proper solvent (e.g., water), and in case a cell-containing aqueous cultured broth is employed, the broth itself serves as the solvent. The suitable concentration range of xylostasin in the phosphorylation system is from about 0.01 to about 100 mg. per milliliter and the amount of cells is from about 1 to about 50 mg. per milliliter on the basis of the weight equivalent to wet intact cells. The amount of a phosphate donor in the system is usually from about 0.1 to about 10 mol., preferably from about 0.8 to about 4 mol. relative to one mole xylostasin. The phosphorylation is carried out at a temperature from about 15°C to 80°C and, preferably, from 20°C to 60°C and most desirably, from 30°C to 40°C; at a pH range from about 4 to 11 and, preferably, 6 to 10. The reaction period is 10 minutes to 48 hours and, preferably, 1 to 48 hours. The above-mentioned phosphate donor includes, among others, nucleoside polyphosphate compounds such as adenosine triphosphate, adenosine diphosphate, etc., deoxynucleoside polyphosphate compounds such as deoxyadenosine triphosphate, deoxyadenosine diphosphate, etc., phosphoenolpyruvic acid, etc. If desired, it is permissible to add a reaction promotor, enzyme stabilizer, etc., to the reaction system. The reaction promotor includes, for example, potassium chloride, sodium chloride, ammonium chloride, lithium chloride, 2-mercaptoethanol, dithiothreitol, cysteine, etc. The enzyme stabilizer includes, for example, mannitol, sorbitol, glycerin, ammonium sulfate, sucrose, etc. Further, if desired, the reaction can be caused to proceed more advantageously by adding a metallic salt such as magnesium chloride, magnesium sulfate, magnesium acetate, manganese chloride, copper acetate, cobalt chloride, zinc chloride or the like.

After the reaction has been completed, the objective compound can be recovered by procedures which are known per se such as column chromatography on, for example, ion exchange resins, ion exchange celluloses, activated carbon, etc., or, after conversion to various salts such as Reinecke's salt, by solvent extraction, solvent precipitation, etc.

The xylostasin phosphate ester thus obtained can be converted to a compound corresponding to the xylostasin phosphate ester whose phosphoric ester residue has been replaced by halogen, i.e. a halogenodeoxy-xylostasin, by first permitting a silylating agent (e.g. hexamethylenedisilazane) or an acylating agent (e.g. acetic anhydride) to act upon the ester to protect its hydroxyl and amino groups and then subjecting the same compound to a halogenation reaction. The halogenation product can then be subjected to an unmasking reaction (a reaction leading to the removal of protective groups) and a reduction reaction to obtain deoxy-xylostasin. Halogenodeoxy-xylostasin and deoxy-xylostasin which can thus be obtained are prominently inhibitory to gram-positive, gram-negative and acid-fast bacteria and, also, to those gram-positive, gram-negative and acid-fast strains of bacteria which are resistant to aminoglycoside antibiotics, thus being useful as, for example, anti-Pseudomonas agents, dysentery remedies and anti-Staphylococcal agents. Each of these compounds can be administered, either as it is or along with a pharmacologically acceptable inert vehicle, in such dosage forms as parenteral injections at the normal daily dosage level of 50 to 200 mg. for adult humans. Thus, the xylostasin phosphate esters obtainable according to this invention are of use as synthetic intermediates which can be converted to useful compounds like the above-mentioned compounds.

Reference Example 1 (Preparation of xylostasin)

A. In 250 ml. of a 0.5 N aqueous solution of barium hydroxide is dissolved 5.0 g. of butirosin A and the solution is boiled on reflux for 2 hours. After cooling, the solution is neutralized with 1N sulfuric acid and the precipitated barium sulfate is removed by centrifugation. The supernatant is run onto a column (2.2 cm × 35 cm) of a cation exchange resin [Amberlite CG-50($NH_4^+$-form)] and, after washing with water, elution is carried out with 0.2N aqueous ammonia, whereupon xylostasin emerges in 700 ml. to 1,100 ml. fractions. The eluate is concentrated to dryness under reduced pressure. The described procedure yields 3.8 g. white powders of xylostasin.

Elemental analysis: C, 44.23; H, 7.53; N, 12.10 %. Calcd. (for $C_{17}H_{34}N_4O_{10}$): C, 44.93; H, 7.54; N, 12.33 %. $[\alpha]_D^{21}$+ 34°(c=1, $H_2O$).

B. Bacillus Y-399, a xylostasin-producing strain [FERM-P-1479, IFO 13321, ATCC 21932] as grown on a glycerin-bouillon-agar slant is used to inoculate a fluid medium (pH 7.2) containing 3 % of polypeptone, 1% of meat extract and 0.5 % of sodium chloride and the inoculated medium is incubated under shaking at 28°C for 40 hours to prepare a seed culture. This seed culture is inoculated, at the inoculation rate of 10 %, into a 50-liter tank containing 30 l. of fermentation medium (pH 7.5) comprising 1 % of glucose, 1 % of polypeptone, 0.7 % of meat extract and 0.5 % of magnesium chloride, and cultivation is carried out at 28°C, 100 % aeration and 200 r.p.m. for 66 hours.

The resultant culture broth is adjusted to pH 1–2 by the addition of a saturated aqueous solution of oxalic acid and filtered with the addition of 300 g. of Hyflo-Super-Cel(Johns-Manville Products) as a filter aid. The resultant filtrate is adjusted to pH 7 and run onto a column packed with 2 liters of a cation exchange resin [Amberlite IRC-50($NH_4^+$-form)], whereupon the active compound is adsorbed on the ion exchange resin. The resin is washed with water and, then, elution is carried out with 5 % aqueous ammonia. The active fraction (2.5 l.) of the eluate is further run onto a column packed with 600 ml. of chromatographic activated carbon to absorb the active material.

After the column is rinsed with water, the active material is eluted with 0.3N hydrochloric acid and the active fractions are pooled. The eluate thus obtained is neutralized by running through Amberlite (Rohm and Haas Co.) IR 45 ($OH^-$-form) column and concentrated under reduced pressure. The concentrate is lyophilized.

The described procedure yields 5.6 g. of a crude xylostasin-containing product (xylostasin content: 30 %, approx.).

REFERENCE EXAMPLE 2 (Conversion of phosphoryl xylostasin to end product 3'-deoxy-xylostasin)

In a sealed tube, 1,000 mg. of xylostasin-3'-phosphate ·2$H_2O$, 700 mg. of triphenylphosphine, 9 ml. of trimethylsilyl chloride, 4 ml. of hexamethyldisilazane and 7.5 ml. of pyridine are heated at 110°C for 43.5 hours.

Under cooling with ice, the reaction mixture is added to 200 ml. of methanol, and the mixture is concentrated to dryness under reduced pressure. Following the addition of 200 ml. of distilled water, the precipitate is recovered by filtration. The recovered precipitate is dissolved in 100 ml. of ethyl acetate and washed with water. The water layer is partially concentrated under reduced pressure and the partial concentrate is pooled with the filtrate previously obtained. The solution is further run onto a column packed with 185 ml. of a cation exchange resin [Amberlite IRC-50($NH_4^+$-form)] and, after washing with water, elution is carried out with 1,000 ml of 1N $NH_4OH$. The eluate is concentrated under reduced pressure to about 100ml. and the concentrate is adsorbed on 275 ml. of Amberlite CG-50 ($NH_4^+$-form). After the resin is washed with water, fractional elution is carried out by the linear gradient method using 1,000 ml. of distilled water and 1,000 ml. of $0.3N_4OH$. The eluate is concentrated under reduced pressure and lyophilized. The described procedure yields 505 mg. of 3'-chloro-3'-deoxy-xylostasin $2H_2O$.

Optical rotation $[\alpha]_D^{24} = +29.7°$ ($H_2O$, c=0.6)

Elemental analysis (for $C_{17}H_{33}N_4O_9Cl \cdot 2H_2O$): Calcd. C, 40.12; H, 7.33; N, 11.01; Cl, 6.97. Found C, 40.08; H, 7.29; N, 10.73; Cl, 6.55.

Thin-layer chromatography, Rf:0.41; xylostasin 0.23 (Developer solvent system= a 5:3 mixture of the upper layer of $CHCl_3$:MeOH:aqueous ammonia:$H_2O$ = 4:3:2:1 and MeOH).

In 20 ml. of $H_2O$ is dissolved 200 mg. of 3'-chloro-3'-deoxy-xylostasin, and with the addition of 2.5 ml. of Raney nickel and 0.3 ml. of triethylamine, the solution is swirled in a current of hydrogen gas at atmospheric temperature and pressure. After 6 hours, the catalyst is filtered off. Then, the catalyst is washed well with 150 ml. of 1N $NH_4OH$ and the washings are pooled with the solution previously obtained. The solution is concentrated to about 20 ml.

The insolubles that have separated out are removed by filtration and the filtrate is run onto a column packed with 30 ml. of a cation exchange resin [Amberlite CG-50 ($NH_4^+$-form)]. After the resin is washed with water, purification elution is carried out with 0.1-0.5N $NH_4OH$(gradient method).

The described procedure yields 152 mg. of 3'-deoxy-xylostasin.

Elemental analysis (for $C_{17}H_{34}N_4O_9 \cdot 3H_2O$): Calcd. C, 41.54; H, 8.18; N, 11.37. Found C, 41.23; H, 7.95; N, 11.08.

Optical rotation $[\alpha]_D^{24} = +28.0°$(c=0.61, $H_2O$).

Thin-layer chromatography, Rf: 0.26; xylostasin:0.2-3(A 5:3 mixture of the upper layer of $CHCl_3$-MeOH-aqueous ammonia-$H_2O$=4:3:2:1 and MeOH is used as developer solvent). In the following examples the relationship between part(s) by weight and part(s) by volume is the same as that between gram(s) and milliliter(s).

EXAMPLE 1

*Escherichia coli* No.R11, a xylostasin-resistant strain is inoculated into 200 parts by volume of a medium (pH 7.4) comprising 0.3% of glucose, 0.5 % of sodium chloride, 1 % of meat extract and 1 % of polypeptone, and the inoculated medium is incubated at 37°C for 16 hours. The culture is further used to inoculate 1,800 parts by volume of a medium of the same composition as above, and cultivation is continued at 37°C for 20 hours. The resultant broth is centrifuged to collect the cells, whereby 8.8 parts by weight of cells are obtained on a wet basis.

These cells are suspended in 35.2 parts by volume of 0.05 M phosphate buffer (pH 7.0) and disrupted by ultrasonication (by means of Kaijyo Denki K.K. Model 4280, 2 amperes, 5 minutes) to obtain a crude enzyme solution. To 35 parts by volume of this crude enzyme solution (protein content:13.3 mg./ml.) are added 5 parts by weight of xylostasin, 50 parts by volume of 0.5 M phosphate buffer (pH 7.0), 50 parts by volume of a 0.1 M aqueous solution of magnesium chloride and 100 parts by volume of a 0.1 M aqueous solution of adenosine triphosphate (adjusted to pH 7.0) to make a total of 500 parts by volume and the reaction is allowed to take place at 37°C for 20 hours.

Then, the reaction is terminated by heating at 80°C for 5 minutes and the resultant precipitate is removed.

Microbiological assay of this reaction for unreacted xylostasin reveals that the reaction has progressed more than 99 %.

The solution is run onto a column of alkali-equilibrated activated carbon (500 parts by volume) and after the column is washed with water, elution is carried out with 0.1N hydrochloric acid. The xylostasin phosphate ester fractions are pooled and further passed over Amberlite IR 40($OH^-$ form, 1000 parts by volume), an anion exchange resin, to remove the chloride ion and, then, concentrated under reduced pressure.

The concentrate is passed over Amberlite CG 50 ($NH_4^+$-form, 200 parts by volume), a cation exchange resin, and after the resin is washed with water, elution is carried out with 0.3N aqueous ammonia. The xylostasin phosphate ester fractions are pooled and concentrated under reduced pressure. The insolubles formed during concentration are removed and the concentrate is lyophilized, whereupon 4.36 parts by weight of a white powder is obtained.

Chemical analysis shows that this produce is xylostasin-3'-phosphate·$H_2O$, the pure yield being 63.6 %.

Elemental analysis, for $C_{17}H_{35}N_4O_{13}P \cdot H_2O$ Calcd. C, 36.96; H. 6.75; N, 10.14; P, 5.61 Found C, 37.52; H, 6.73; N, 9.78; P, 5.41 .

$[\alpha]_D^{24} = +40.0°$(c=0.60, $H_2O$).

$IR\nu_{max}^{KBr}$ $cm^{-1}$ : 968

EXAMPLE 2

*Pseudomonas aeruginosa* No. R34R, a xylostasin-resistant strain is inoculated into 800 parts by volume of a medium (pH 7.2) comprising 0.5 % of polypeptone, 0.3 % of meat extract and 0.5 % of yeast extract and grown at 37°C for 16 hours. The resultant culture is transferred to 7.2 liters of a medium of the same composition as above and the inoculated medium is incubated at 37°C for 2 hours. The resultant culture broth is centrifuged to harvest the cells. The procedure yields 17.6 parts by weight of cells on a wet basis.

The cells are suspended in 100 parts by volume of 0.5M tris-HCl buffer (pH8.0) and, then, 100 parts by volume of a 1M aqueous solution of potassium chloride, 200 parts by volume of a 0.1M aqueous solution (adjusted to pH 8.0) of adenosine diphosphate, 100 parts by volume of a 0.1M aqueous solution of 2-mercaptoethanol, 100 parts by volume of a 1M aqueous solution of magnesium chloride and 1 part by weight of xylostasin are added. The mixture is made up to a total of 1000 parts by volume and gently stirred to react at 37°C for 20 hours. After the reaction the mixture is centrifuged to remove the cells and the supernatant is taken. Microbiological assay of this supernatant for unreacted xylostasin shows that the reaction has progressed at least 99 %.

The solution is then passed over Amberlite IRC-50 (NH$_4^+$-form, 200 parts by volume), a cation exchange resin, and after the resin is washed with water, elution is performed with 0.5N aqueous ammonia. The xylostasin phosphate ester fractions are pooled and concentrated and the concentrate is further passed over CM-Sephadex (Pharmacia) C25(NH$_4^+$-form, 500 parts by volume), a cation exchanger. After washing with water, elution is carried out with 0.03N aqueous ammonia.

The xylostasin phosphate ester fractions are pooled, concentrated and lyophilized to obtain 1.07 parts by weight of a white powder.

Chemical analysis reveals that the product is xylostasin 5''-phosphate H$_2$O, the pure yield being 78%.

Elemental analysis, for C$_{17}$H$_{35}$N$_4$O$_{13}$P·H$_2$O: Calcd. C, 36.96; H, 6.75; N, 10.14; P, 5.61. Found C, 36.93; H, 6.59; N, 10.06; P, 5.02.

$[\alpha]_D^{24} = +35.1°(c=0.62, H_2O)$.

IR$\nu_{max}^{KBr}$ cm$^{-1}$ = 965

What we claim is:

1. A compound selected from the group consisting of compounds of the formula

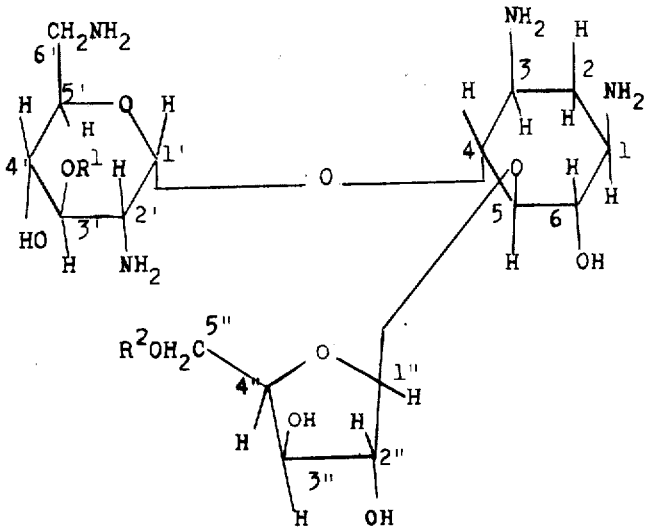

wherein R$^1$ and R$^2$, independently of each other, represent hydrogen or phosphono, with the proviso that R$^1$ and R$^2$ are not both hydrogen.

2. The compound according to claim 1, wherein R$^1$ represents phosphono and R$^2$ represents hydrogen.

3. The compound according to claim 1, wherein R$^1$ represents hydrogen and R$^2$ represents phosphono.

* * * * *